United States Patent
Bala

(10) Patent No.: US 10,704,077 B2
(45) Date of Patent: Jul. 7, 2020

(54) STERILIZATION INDICATOR WITH TEMPERATURE INDICATOR

(71) Applicant: American Sterilizer Company, Mentor, OH (US)

(72) Inventor: Harry Bala, South Barrington, IL (US)

(73) Assignee: American Sterilizer Company, Mentor, OH (US)

( * ) Notice: Subject to any disclaimer, the term of this patent is extended or adjusted under 35 U.S.C. 154(b) by 295 days.

(21) Appl. No.: 15/657,891

(22) Filed: Jul. 24, 2017

(65) Prior Publication Data
US 2019/0024137 A1    Jan. 24, 2019

(51) Int. Cl.
C12Q 1/22        (2006.01)
G01N 31/22       (2006.01)
A61L 2/28        (2006.01)

(52) U.S. Cl.
CPC .............. *C12Q 1/22* (2013.01); *A61L 2/28* (2013.01); *G01N 31/226* (2013.01)

(58) Field of Classification Search
CPC ............ C12Q 1/22; A61L 2/28; G01N 31/226
See application file for complete search history.

(56) References Cited

U.S. PATENT DOCUMENTS

| | | | |
|---|---|---|---|
| 3,313,266 A | 4/1967 | Kelson | |
| 3,341,238 A | 9/1967 | White | |
| 3,568,627 A * | 3/1971 | Selinger | G01K 3/04 116/207 |
| 3,652,249 A | 3/1972 | White | |
| 3,981,683 A | 9/1976 | Larsson et al. | |
| 4,448,548 A | 5/1984 | Foley | |
| 9,354,227 B2 | 5/2016 | Bala et al. | |
| 9,623,134 B1 | 4/2017 | Bala | |
| 2010/0012018 A1 | 1/2010 | Ribi | |
| 2015/0253311 A1* | 9/2015 | Bala | G01N 33/525 422/423 |

FOREIGN PATENT DOCUMENTS

JP    2010220970 A    10/2010

OTHER PUBLICATIONS

International Search Report and Written Opinion issued by International Searching Authority in connection to PCT/US2018/028490 dated Jun. 26, 2018.

* cited by examiner

*Primary Examiner* — Dennis White
(74) *Attorney, Agent, or Firm* — Levenfeld Pearlstein, LLC

(57) ABSTRACT

A steam sterilization indicator for indicating acceptability of a sterilization cycle includes a temperature indicator for indicating the temperature used in the sterilization cycle.

18 Claims, 2 Drawing Sheets

STERILIZATION INDICATOR WITH TEMPERATURE INDICATOR

BACKGROUND OF THE INVENTION

It is well known that heat destroys microorganisms. The presence of moisture accelerates this destruction by denaturing or coagulating the proteins making up the microorganisms. Most microorganisms contain sufficient water so that moderate heat alone, e.g. 80° C.-100° C., will destroy the microorganism. Many bacterial spores, on the other hand, contain substantially no water and require elevated temperatures, in excess of 150° C., for their destruction where dry heat is used. Hence, the destruction of such organisms is generally carried out in the presence of steam in autoclaves.

Chemical indicators have been developed to indicate whether an acceptable level of sterilization was achieved in a sterilization cycle. One such product is known as Temp-Tube, and is disclosed in, for example, Kelson, U.S. Pat. No. 3,313,266, White, U.S. Pat. No. 3,341,238, and White, U.S. Pat. No. 3,652,249. The device consists of a sealed tube containing a compound with a melting point which corresponds to the sterilization temperature. The device is capable of indicating whether or not the autoclave was held at a temperature above or below the melting point for a period of time once the melting point is reached.

Other sterility indicators are known. One such indicator is disclosed in Larsson, U.S. Pat. No. 3,981,683, and uses a backing strip of aluminum foil having an organic compound containing oxygen or nitrogen in contact with a wicking strip, and a cover strip overlying the organic compound and the wicking strip. The cover strip is a polymeric rate controlling film that permits water vapor to pass through at a rate sufficient to make the strip operable at a temperature to be monitored. Foley, U.S. Pat. No. 4,448,548 also discloses a steam sterilization indicator.

Further, Class 5/Type 5 sterilization indicators, which are configured to react to three critical sterilization parameters, i.e. time, temperature and the presence of steam, of sterilization cycles are available. Class 5/Type 5 indicators are configured such that their performance correlates to a biological indicator (BI). A Class 5/Type 5 indicator may be configured to work for more than one sterilization condition. For example, a Class 5/Type 5 indicator may be configured for a steam sterilization cycle at 121° C. for 30 minutes or a steam sterilization cycle at 132° C. for 4 minutes.

Class 6 sterilization indicators, which are configured to react to the three critical sterilization parameters for a specified sterilization cycle, are also available. U.S. Pat. No. 9,623,134, which is assigned to the Applicant of the present application and incorporated herein by reference, discloses sterilization test strips configured to indicate whether an acceptable level of steam sterilization has occurred after a predetermined period of time at a predetermined temperature. For example, a test strip may be configured to indicate whether an acceptable level of steam sterilization has occurred after 4 minutes at 134° C. However, these test strips are configured to work for one specific steam sterilization condition (e.g. 4 minutes at 134° C.) Thus, a different test strip is required for each different sterilization condition. For example, the test strip configured for a steam sterilization cycle at 132° C. for 4 minutes will not properly indicate for a steam sterilization cycle at 121° C. 12 minutes. As such, users who perform sterilization processes in multiple different conditions are forced to purchase and stock multiple different test strips, which can increase operation costs and lead to user errors in selecting a correct indicator.

U.S. Pat. No. 9,354,227, which is also assigned to the Applicant of the present application and incorporated herein by reference, discloses a dual sterilization indicator configured to work for two different sterilization conditions. The dual indicator includes two pass zones, each of which is configured for indicating acceptability of a sterilization cycle at a different sterilization condition. As such, the dual indicator may replace two different Class 6 sterilization indicators, and thus, can reduce a number of different test indicators required for users.

The dual indicator is configured for two different sterilization conditions. Further, Class 5/Type 5 indicators may be used for more than one sterilization conditions. Thus, these indicators may present a risk of confusion in determining the sterilization condition used for a steam sterilization cycle. Therefore, there is a need for an improved indicator that can provide an indication of sterilization conditions used in a sterilization cycle along with indication of acceptability of the sterilization cycle.

BRIEF SUMMARY OF THE INVENTION

A dual sterilization indicator for indicating acceptability of a sterilization cycle is configured to work for two different sterilization conditions and includes a temperature indicator to assist a user in determining which of the two sterilization conditions is used in the sterilization cycle.

In one aspect, a sterilization indicator is configured for indicating acceptability of a sterilization cycle for at least two different sterilization conditions including a first sterilization condition for a first period of time at a first temperature and a second sterilization condition for a second period of time at a second temperature that is different from the first temperature. The sterilization indicator may include a base element, an indicator chemical composition arranged on the base element, a wicking material positioned at least in part in contact with the indicator chemical composition, and a film layer positioned over the base element, the wicking material, and the indicator chemical composition. The sterilization indicator may also include a first pass zone, a second pass zone, and a temperature indicator configured to indicate a temperature used in a sterilization cycle.

Further, the sterilization indicator may be configured to indicate that an acceptable level of sterilization has occurred when the indicator chemical composition wicks along the wicking material to a location within the first pass zone after a sterilization cycle using the first sterilization condition, or when the indicator chemical composition wicks along the wicking material to a location within the second pass zone after a sterilization cycle using the second sterilization condition. The temperature indicator may be configured to display a base color at a room temperature and change to a first color after being exposed to the first temperature or change to a second color after being exposed to the second temperature, in which the first color is visually distinguishable from the base color, and the second color is visually distinguishable from the base color and the first color.

In some embodiments, the base element may be formed from a thermally conductive material having a length and a width, and may include a recess formed therein extending along about a longitudinal centerline thereof. The recess may be formed within the base material less than the length and the width of the base material. Further, the sterilization indicator may include a first adhesive layer disposed on the base element. The indicator chemical composition may be deposited in the recess, and the wicking material may be positioned at least in part within the recess. The wicking material may extend less than the length and width of the base element. Further, the sterilization indicator may also include a paper layer disposed over the film layer, and a second adhesive layer disposed between the paper layer and the film layer. The paper layer and the second adhesive layer may include a window therein.

In an embodiment, the temperature indicator may be printed on the paper layer using a thermochromic ink. Further, the sterilization indicator may also include at least one color standard displaying the first color and the second. In such an embodiment, a user may compare the temperature indicator against the at least one color standard to determine a temperature used in a sterilization cycle. In some embodiments, the at least one color standard may include a first color standard displaying the first color with a reference to the first temperature, and a second color standard displaying the second color with a reference to the second temperature.

In another embodiment, the temperature indicator may be printed using an irreversible thermochromic ink that gradually changes color over a range of temperatures. In such an embodiment, the at least one color standard may include a color scale displaying the gradual color change of the irreversible thermochromic ink over a temperature range including the first temperature and the second temperature. The color standard may include references to at least the first temperature and the second temperature.

In an embodiment, the indicator chemical composition may contain a temperature sensitive material and a dye. Further, the film may be formed from a cast polypropylene, such as a cast polypropylene having a thickness of about 0.9 to 1.1 mils, about 2.0 to 2.2 mils, or about 3.0 to 3.2 mils. The base element may be formed from aluminum having a thickness of about 3 mils. The first adhesive layer may be formed from an acrylic adhesive, and the second adhesive layer may also be formed from an acrylic adhesive.

Further, the paper layer may include a first marker and a second marker, in which the first marker is longitudinally spaced from the indicator chemical composition with a first distance therebetween, and the second marker is longitudinally spaced from the indicator chemical composition with a second distance therebetween. The second distance may be greater than the first distance, such that the first pass zone is defined by the location of the first marker and an area beyond the first marker, and the second pass zone is defined by the second marker and an area beyond the second marker. In such embodiments, the first temperature may be 121° C. and the first time may be selected from 12 minutes, 15 minutes, 20 minutes, and 30 minutes. The second temperature may be 132° C. and the second period of time may be 4 minutes, or the second temperature may be 134° C. and the second period of time may be selected from 3.5 minutes, 4 minutes, 5 minutes and 7 minutes, or the second temperature may be 135° C. and the second period of time may be 3 minutes.

In another embodiment, the sterilization indicator may also include a third marker, in which the first pass zone is defined by an area between the first marker and the second marker, and the second pass zone is defined by an area between the second marker and the third marker. The sterilization indicator may be configured to indicate an acceptable level of sterilization after a sterilization cycle using the first sterilization condition when the indicator chemical composition wicks to a location within the first pass zone and does not wick beyond the second marker. In such an embodiment, at least a portion of the first pass zone may be colored with the first color, and at least a portion of the second pass zone may be colored with the second color.

Further, the film layer may be formed from a cast polypropylene having a thickness of about 2.2 mil, and the wicking material may be formed from a wicking paper having a basis weight of about 87.7 g/m$^2$ and a thickness of about 7.5 mil. The first sterilization condition may be selected from 12 minutes at 121° C., 15 minutes at 121° C., 20 minutes at 121° C., 30 minutes at 121° C., and the second sterilization condition may be selected from 4 minutes at 132° C., 3.5 minutes at 134° C., 4 minutes at 134° C., 5 minutes at 134° C., 7 minutes at 134° C., and 3 minutes at 135° C. Alternatively, the film layer may be formed from a cast polypropylene having a thickness of about 2.2 mil, and the wicking material may be formed from a wicking paper having a basis weight of about 66 g/m$^2$ and a thickness of about 7.3 mil, wherein the first temperature is 121° C. and the first period of time is 12, 15, 20, or 30 minutes, and the second temperature is 132° C. and the second period of time is 4 minutes.

In another aspect, a steam sterilization indicator configured as a Class 5/Type 5 steam sterilization indicator is provided. The steam sterilization indicator includes a base element, an indicator chemical composition arranged on the base element, a wicking material positioned at least in part in contact with the indicator chemical composition, a film layer positioned over the base element, the wicking material and the indicator chemical composition, a pass zone, a fail zone, and a temperature indicator formed from an irreversible thermochromic ink configured to indicate a temperature of a sterilization cycle.

In yet another aspect, a sterilization record card including a temperature indicator formed from an irreversible thermochromic ink is provided.

These and other features and advantages of the present indicator will be apparent from the following detailed description, in conjunction with the appended claims.

BRIEF DESCRIPTION OF THE SEVERAL VIEWS OF THE DRAWINGS

The benefits and advantages of the present device will become more readily apparent to those of ordinary skill in the relevant art after reviewing the following detailed description and accompanying drawings, wherein.

DETAILED DESCRIPTION

Figure 1:
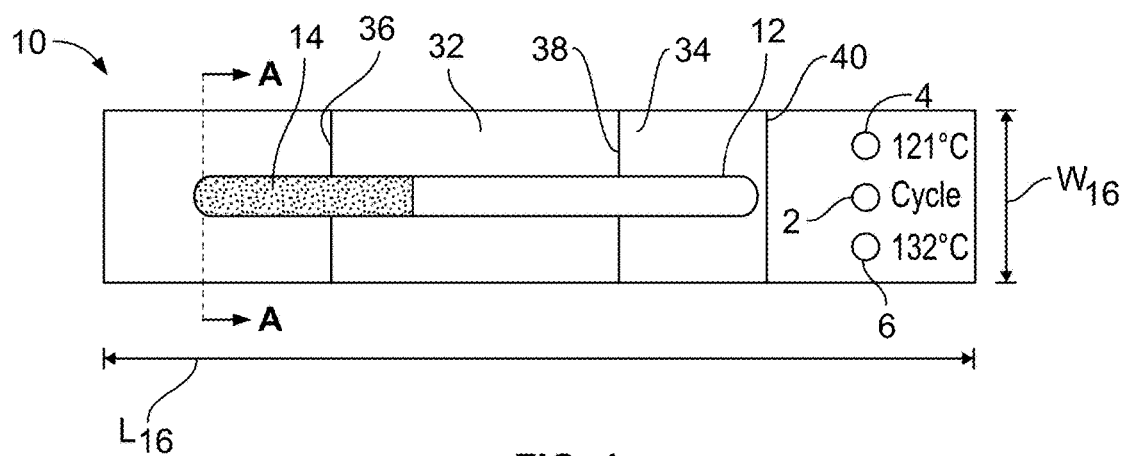
FIG. 1 is a top plan view of a dual steam sterilization indicator including a temperature indicator according to an embodiment.

While the present device is susceptible of embodiment in various forms, there is shown in the drawings and will hereinafter be described a presently preferred embodiment with the understanding that the present disclosure is to be considered an exemplification of the device and is not intended to be limited to the specific embodiments illustrated.

Figure 2:
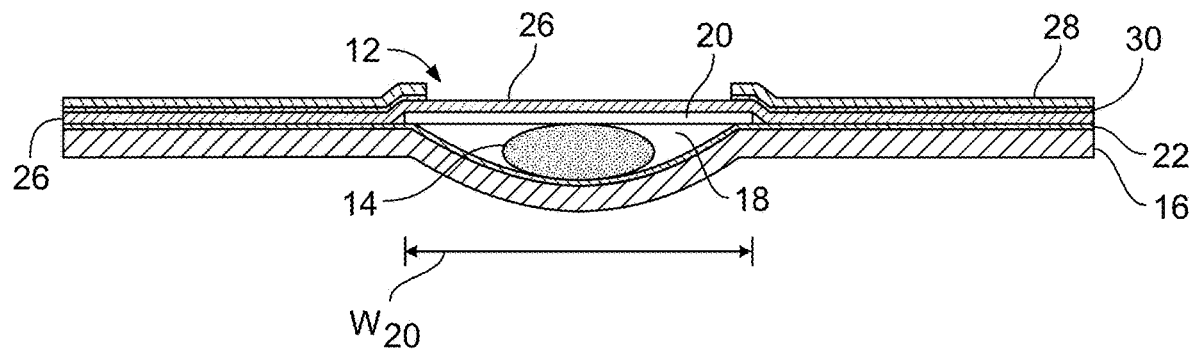
FIG. 2 is a cross-sectional view taken along line A-A of FIG. 1.
Figure 3:
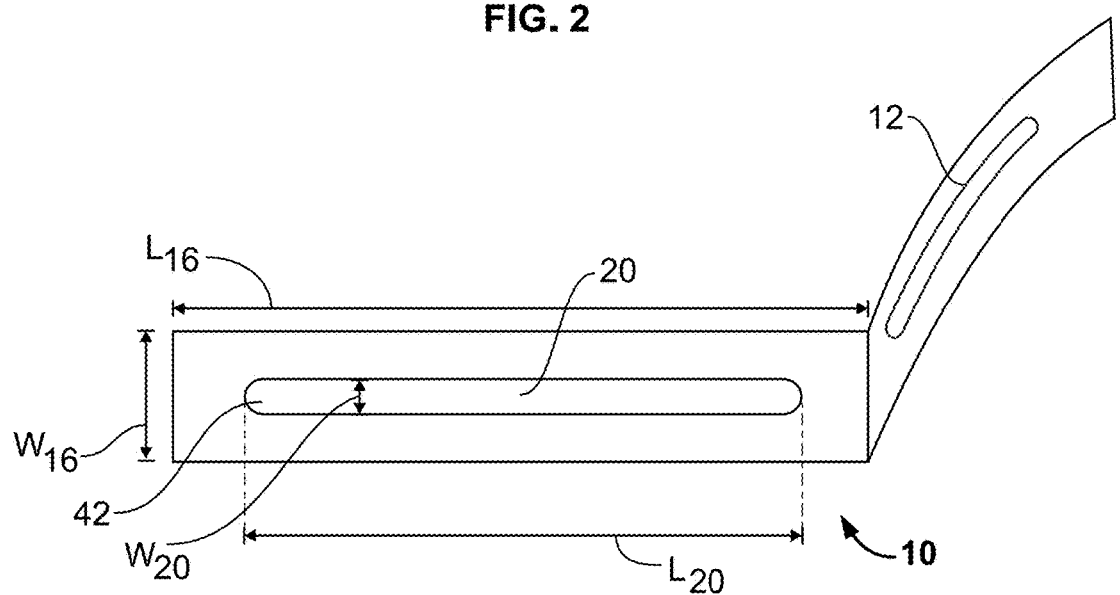
FIG. 3 is a top perspective view of the dual steam sterilization indicator of FIG. 1 with a paper layer, a second adhesive layer, and a film layer peeled off.

Referring to FIGS. 1-3, an embodiment of a dual sterilization indicator 10 including a temperature indicator 2 is shown. The dual indicator 10 includes an open window 12 through which the wicking of an indicator chemical composition 14 may be observed to determine whether an acceptable level of sterilization has occurred as will be described below. As shown, the dual indicator 10 includes two pass zones 32, 34, each of which is configured for indicating whether an acceptable level of steam sterilization has occurred for a different sterilization condition. For example, the dual indicator 10 may be configured to properly indicate a steam sterilization cycle at 121° C. for 12 minutes and a steam sterilization cycle at 134° C. for 4 minutes. Further, the dual indicator 10 may include a temperature indicator 2 for indicating the temperature used for a sterilization cycle.

In an embodiment, a first pass zone 32 may be defined by the location of a first marker 36 and the area beyond the first marker 36. Similarly, a second pass zone 34 may be defined by a second marker 38, and the area beyond the second marker 38. The dual indicator 10 may be configured to have various length and width. For example, the dual indicator 10 may be configured to have a length of about 1.5 inches to about 5 inches, preferably about 2 inches to about 4 inches, and more preferably about 4 inches, and a width of about ⅝ inches to about 1 inch, and preferably about ¾ inches.

FIG. 2 is a cross-sectional illustration of the dual indicator 10 of FIG. 1. The dual indicator 10 may generally include a base element 16, a first adhesive layer 22, a wicking element 20, a film layer 26, a second adhesive layer 30, a paper layer 28, and an indicator chemical composition 14. The base element 16 may be formed from a foil, for example, an aluminum foil, or other high-heat transfer material. The first adhesive layer 22 may be disposed on the base element 16 as a continuous layer covering substantially the entire top surface of the base element 16. The base element may have a length $L_{16}$ and width $W_{16}$. A depression 18 may be formed in the base element 16 and the first adhesive layer 22. The indicator chemical composition 14 may be provided in the recess 18 between the first adhesive layer 22 and the wicking element 20.

The wicking element 20 may be disposed on the first adhesive layer 22, and over the indicator chemical composition 14, such that the wicking element 20 may be in contact with the indicator chemical composition 14. FIG. 3 is a perspective top view of the dual indicator 10 with the film layer 26, the second adhesive layer 30, and the paper layer 28 peeled away. As shown, the wicking element 20 has a width $W_{20}$ and a length $L_{20}$ that is less than the width $W_{16}$ and the length $L_{16}$ of the base element 16. For example, the wicking element 20 may be configured to have a width $W_{20}$ of about ⅛ inches to about ⅜ inches, preferably about ¼ inches, and the base element 16 may be configured to have a width $W_{16}$ of about ⅝ inches to about 1 inch, preferably about ¾ inches. The wicking element 20 may be generally centered on the base element 16 and over the indicator chemical composition 14 in the recess 18, such that an end portion 42 of the wicking element 20 may be in contact with the indicator chemical composition 14. The wicking element 20 may extend longitudinally along the base element 16, such that at least some portion of the wicking element 20 is securely attached to the base element 20 by the first adhesive layer 22. In this manner, the indicator chemical composition 14 and the wicking element 20 are bounded within the four sides of the dual indicator 10.

A film layer 26 may be applied over the base element 16, indicator chemical composition 14, and wicking element 20, and may be adhered to the base element 16 by the first adhesive layer 22. The film layer 26 may be a transparent film, as will be discussed in more detail below. The paper layer 28 and the second adhesive layer 30 may be disposed over the film layer 26. The paper layer 28 and adhesive layer 30 may include the window 12 that is cut out (as seen in FIG. 1) to allow for visual inspection within the window 12, through the film layer 26.

In an embodiment, the base element 16 may be formed from an aluminum foil, and a layer of an acrylic adhesive may be coated on the base element 16 to form the first adhesive layer 22. In some embodiments, a foil adhesive label having a ³⁄1000 inch (3 mil) thickness may be used to form the base element 16 and the first adhesive layer 22. Further, an adhesive coated paper may be used to form the paper layer 28 and the second adhesive layer 30. For example, an acrylic adhesive coated paper may be used to form the paper layer 28 and the second adhesive layer 30. The film layer 26 may be formed from a cast polypropylene film having a thickness of about 0.9 to 1.1 mils, about 2.0 to 2.2 mil, or about 3.0 to 3.2 mil.

The wicking element 20 may be formed from a suitable wicking material. In some embodiments, the wicking element 20 may be formed from a wicking paper having a basis weight of about 66 grams per square meter ($g/m^2$) to about 186 $g/m^2$, and a caliper or thickness of about 7.5 thousandths of an inch (mil) to about 13.3 mil. For example, the wicking element 20 may be formed from a low-ash, qualitative paper having a basis weight of about 66 $g/m^2$ and a thickness of about 7.3 mil, or a low-ash, qualitative paper having a basis weight of about 87.7 $g/m^2$ and a thickness of about 7.5 mil, or from a white, smooth surface, cotton paper having a basis weight of about 186 $g/m^2$ and a thickness of about 13.3 mils. The indicator chemical composition 14 may be formed from a temperature sensitive chemical composition. The indicator chemical composition may also contain a colorant in a concentration of about 0.01 percent by weight.

The pass zones 32, 34 may be provided on the dual indicator 10, such that the pass zones 32, 34 are visually available to a user. For example, the pass zones 32, 34 may be provided on the paper layer 28. The first pass zone 32 may be defined by the location of the first marker 36 and the area beyond the first marker 36, while the second pass zone 34 may be defined by the second marker 38 and the area beyond the second marker 38. In use, the indicator chemical composition liquefies and wicks along the wicking material 20 when exposed to steam during a sterilization process. At the end of the sterilization process, a user can determine whether an acceptable level of sterilization has occurred by inspecting how far the liquefied indicator chemical composition 14 has moved along the wicking material 20 through the window 12.

For example, the dual indicator 10 may be used for a sterilization cycle for a first period of time at a first temperature (e.g. 12 minutes at 121° C.), after which a user may determine whether an acceptable level of sterilization has occurred by inspecting whether the indicator chemical composition 14 has reached the first pass zone 32. That is, if the indicator chemical composition 14 has reached the first marker 36 or a location beyond the first marker 36, it indicates that an acceptable level of sterilization has occurred after the sterilization process for the first period of time at the first temperature. The dual indicator 10 may also be used for a sterilization cycle at a second period of time at a second temperature (e.g. 4 minutes at 134° C.), after which a user may determine acceptability of the sterilization cycle by inspecting whether the indicator chemical composition 14 has reached the second pass zone 34. That is, if the indicator chemical composition 14 has reached the second marker 38 or a location beyond the second marker 38, it indicates that an acceptable level of sterilization has occurred after the sterilization process for the second period of time at the second temperature.

Therefore, the markers 36, 38 are drawn at predetermined or precalculated distances from the location of the indicator chemical composition 14 according to two different sterilization conditions. As such, the dual indicator 10 may be used to determine whether an acceptable sterilization has occurred after a first period of time at a first temperature, or after a second period of time at a second predetermine temperature. In an embodiment, the dual indicator 10 may be configured to properly indicate a first sterilization condition selected from 12 minutes at 121° C., 15 minutes at 121° C., 20 minutes at 121° C., 30 minutes at 121° C., or a second sterilization condition selected from 4 minutes at 132° C., 3.5 minutes at 134° C., 4 minutes at 134° C., 5 minutes at 134° C., 7 minutes at 134° C., and 3 minutes at 135° C.

Further, the dual indicator 10 may include a temperature indicator 2 for indicating the temperature used in a sterilization cycle. The temperature indicator 2 may be formed from a temperature sensitive material, such as an irreversible thermochromic ink that is configured to change color from a base color to a first color after being exposed to a first temperature during a sterilization cycle or change to a second color after being exposed to a second temperature during a sterilization cycle.

For example, in an embodiment in which the dual indicator 10 is configured to properly indicate a first sterilization condition for 12 minutes at 121° C. or a second sterilization condition for 4 minutes at 132° C., the temperature indicator 2 may be configured to change from a base color to a first color after being exposed to a temperature of 121° C., or change from the base color to a second color after being exposed to a temperature of 132° C. As such, by inspecting the temperature indicator 2, a user may determine the sterilization condition used for a sterilization cycle.

In some embodiments, the dual indicator 10 may include color standards to assist a user in determining the temperature indicated by the temperature indicator 2. In the embodiment of FIG. 1, the dual indicator 10 includes two color standards 4, 6. The temperature indicator 2 may be formed using a thermochromic ink, which has a base color, for example, clear, white, or off white, at a room temperature, and changes to a first color, for example, light blue or light turquoise, after being exposed to a first temperature, for example, 121° C., during a sterilization cycle, or changes to a second color, for example, dark blue or dark turquoise, after being exposed to a second temperature, for example, 132° C. In such an embodiment, a first color standard 4 may be formed to display the first color with a reference to the first temperature, and a second color standard 6 may be formed to display the second color with reference to the second temperature. As such, a user can compare the color of the temperature indicator 2 against the color standards 4, 6 to determine a temperature used in a sterilization cycle.

The temperature indicator 2 may be printed on the paper layer 28 using a suitable irreversible thermochromatic ink or paint that changes color from a base color to a first color, which is visually distinguishable from the base color, at a first sterilization condition temperature, and changes to a second color, which is visually distinguishable from the base color and the first color, at a second sterilization condition temperature. Although, the temperature indicator 2 and color standards 4, 6 are arranged on a right side of the dual indicator 10 in FIG. 1, they may be arranged in any suitable location on the dual indicator 10. Further, the indicator 2 and color standards 2, 6 may be provided in any visually suitable sizes and shapes.

Figure 4:
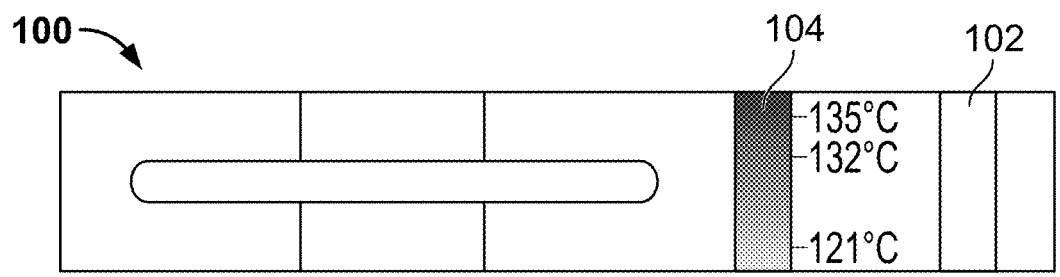
FIG. 4 is a top plan view of a dual steam sterilization indicator including a temperature indicator according to another embodiment.

FIG. 4 shows a dual indicator 100 according to another embodiment. The dual indicator 100 is configured similarly configured to the dual indicator 10 of FIG. 1, except a color scale 104 is provided as color standards. In this embodiment, a temperature indicator 102 may be printed using a thermochromic ink having a base color at a room temperature, which gradually changes color over a temperature range. For example, the temperature indicator 102 may be printed using an irreversible thermochromic ink that gradually changes color from off-white at room temperature to a light turquoise at around 121° C., to a dark turquoise at around 132° C., and becomes darker therebeyond. In such an embodiment, the color scale 104 may be provided to display the gradual color change scale of the irreversible thermochromic ink over a range of temperature with references to at least the first and second temperatures of the first and second sterilization conditions.

In FIG. 4, the color scale 104 includes three markings at 121° C., 132° C., and 135° C. on the color scale 104. In other embodiments, the color scale 104 may be provided with two temperature markings for the two temperatures of the two sterilization conditions that the dual indicator 100 is configured for, or may be provided with more than three temperature markings. In the embodiment, of FIG. 4, the temperature indicator 102 and the color scale 104 are provided parallel to each other extending across the width of the dual indicator 100. In other embodiments, the temperature indicator 102 and the color scale 104 may be provided in any suitable location on the dual indicator 100. In yet another embodiment, the color standards may be provided separately, for example, in the form of a card including different color standards or a color scale.

Referring back to the embodiment of FIG. 1, the dual indicator 10 also may include a third line 40. In such an embodiment, the first pass zone 32 may be defined by the area between the first marker 36 and the second marker 38, and the second pass zone may be defined by the second marker 38 and the third line 40. In such an embodiment, the first pass zone 32 may be colored to display the color of the temperature indicator 2 at a first temperature for a first sterilization condition, while the second pass zone 32 may be colored to display the color of the temperature indicator 2 at a second temperature for a second sterilization condition. For example, the temperature indicator 2 may be printed using an irreversible thermochromic ink having a base color at a room temperature, which changes to a first color, such as light blue, after being exposed to a first temperature, such as 121° C., or changes to a second color, such as dark blue, after being exposed to a second temperature, such as 134° C. Accordingly, the first pass zone may be colored to match the first color, while the second pass zone may be colored to match the second color to assist a user in determining a sterilization cycle condition. In such an embodiment, the color standards 4, 6 may be omitted as the colors in the first and second pass zones 32, 34 may serve as the color standards.

In such an embodiment, an acceptable level of sterilization after a sterilization cycle using a first condition (e.g. 12 minutes at 121° C.) is indicated when the indicator chemical 14 wicks to a location within the first zone 32, as shown in FIG. 1. Although, the indicator chemical 14 may wick beyond the first pass zone 32 and into the second pass zone 34, which also indicates an acceptable level of sterilization after a sterilization process in the first condition, an acceptable level of sterilization after a sterilization process in the first condition will usually fall within the first pass zone 32. Alternatively, the dual indicator 10 can also be used to indicate an acceptable level of sterilization after a sterilization process in a second condition (e.g. 4 minutes at 134° C.), in which an acceptable level of sterilization is indicated when the indicator chemical 14 wicks to a location within the second pass zone 34.

In an embodiment, the dual indicator 10 may be configured such that the chemical composition 14 wicks to a location within the first pass zone 32 and does not wick pass the second marker 38 to indicate that an acceptable level of sterilization has occurred after the first period of time at the first temperature, even if the dual indicator 10 is left in the sterilization condition longer than the first temperature. For example, the dual indicator 10 may be configured to indicate an acceptable level of sterilization after 12 minutes at 121° C. or after 4 minutes at 134° C., in which the indicator chemical composition 14 wicks pass the first marker 36 to a location within the first pass zone 32 to indicate that an acceptable level of sterilization has occurred after 12 minutes at 121° C., and does not wick beyond the second marker 38 even if the dual indicator 10 is left in the sterilization condition at 121° C. for more than 12 minutes, for example 30 minutes. Thus, such a dual indicator 10 can reduce a risk of confusion for users since an acceptable level of sterilization for the first sterilization condition is indicated by the indicator chemical composition 14 wicking to a location within the first pass zone 32, but not beyond the second marker 38.

In an embodiment, the dual indicator 10 is configured to indicate an acceptable level of sterilization after 12 minutes at 121° C. or after 4 minutes at 134° C., and includes the base element 16, the first adhesive layer 22, the wicking element 20, the film layer 26, the second adhesive layer 30, the paper layer 28, and the indicator chemical composition 14, in which the film layer 26 is formed from a cast polypropylene film having a thickness of about 2.2 mil, and the wicking element 20 is formed from a wicking paper having a basis weight of about 87.7 g/m² and a thickness of about 7.5 mil. The porosity of the wicking paper correlates with the basis weight and thickness of the wicking paper.

The dual indicator 10 may also be configured to work for different sterilization conditions by adjusting the placement of the first marker 36 and the placement of the second marker 38. For example, the dual indicator 10 may be configured to work for various first and second sterilization condition combinations, in which the first sterilization condition is selected from 12 minutes at 121° C., 15 minutes at 121° C., 20 minutes at 121° C., 30 minutes at 121° C., and the second sterilization condition is selected from 4 minutes at 132° C., 3.5 minutes at 134° C., 4 minutes at 134° C., 5 minutes at 134° C., 7 minutes at 134° C., and 3 minutes at 135° C.

As such, the dual indicator 10 may be configured to replace two types of Class 6 sterilization indicators for two different sterilization conditions. The dual indicator 10 meets the performance requirements set for Class 6 indictors set by American National Standards Institute (ANSI)/Association for the Advancement of Medical Instrumentation (AAMI)/International Organization for Standards (ISO) 11140.

Figure 5:
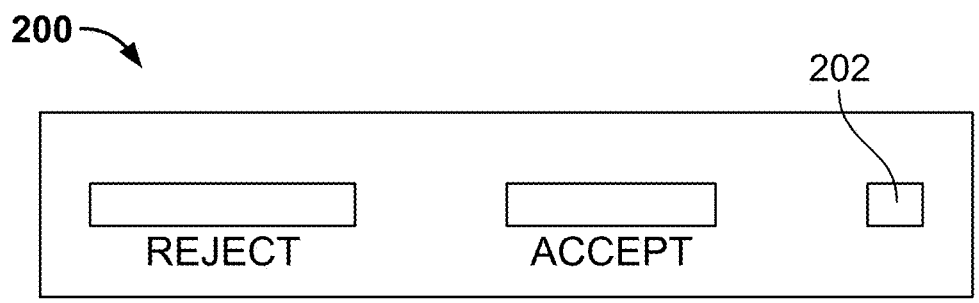
FIG. 5 is a top plan view of a Class 5/Type 5 steam sterilization indicator including a temperature indicator according to an embodiment.

FIG. 5 shows a Class 5/Type 5 steam sterilization indicator 200 including a temperature indicator 202 according to an embodiment. The indicator 200 is similar to known Class 5/Type 5 indicators, such as SteriScan® Class 5/Type 5 Steam Sterilization Integrators available from the Applicant of the present application, except the indicator 200 includes a temperature indicator 202, which may be similarly configured to the temperature indicator 2 or 102 of foregoing embodiments. For example, the temperature indicator 202 may be printed with an irreversible thermochromic ink that gradually changes color from a base color, such as clear, white, or off white at room temperature to a light turquoise at around 121° C., and to a dark turquoise at around 132° C., and becomes darker therebeyond. Color standards may be provided on the indicator 200 or in a separate medium for a user's comparison. The Class 5/Type 5 steam sterilization indicator 200 may be configured to properly indicate across a sterilization temperature range from about 115° C. to about 138° C. Thus, a user may determine the temperature of a steam sterilization cycle by comparing the color of the temperature indicator 202 against the color standards after a steam sterilization cycle.

Figure 6:
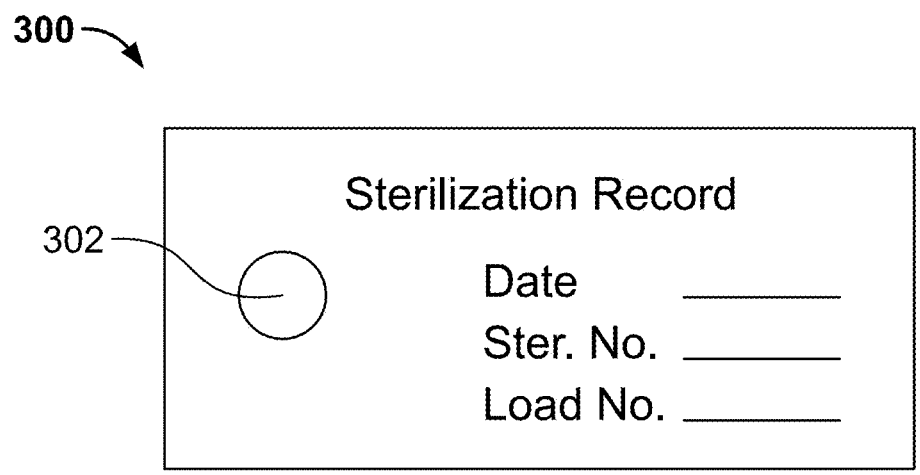
FIG. 6 is an illustration of a sterilization record card including a temperature indicator according to an embodiment.

A temperature indicator for indicating a temperature for a sterilization cycle may be provided in other devices. For example, a sterilization record card for recording information regarding a sterilization cycle may be provided with a temperature indicator as shown in FIG. 6. A sterilization record card 300 may include a temperature indicator 302 configured similar to the temperature indicators 2, 102, 202 of foregoing embodiments along with other information about a sterilization cycle, such as date, sterilization number, and load number. Such a sterilization card 300 may be included in a load for a sterilization cycle. Color standards may be provided on the sterilization card 300 or on a separate card to assist a user to determine a temperature used in a sterilization cycle. In another embodiment, a temperature indicator may be provided on a sterilization pouch for containing medical devices, such as surgical instruments, for a sterilization cycle.

All patents referred to herein, are hereby incorporated herein by reference, whether or not specifically done so within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present disclosure. It is to be understood that no limitation with respect to the specific embodiments illustrated is intended or should be inferred. The disclosure is intended to cover all such modifications as fall within the scope of the disclosure.

What is claimed is:

1. A sterilization indicator configured for indicating acceptability of a sterilization cycle for at least two different sterilization conditions including a first sterilization condition for a first period of time at a first temperature and a second sterilization condition for a second period of time at a second temperature that is different from the first temperature, the sterilization indicator comprising:
   a base element;

an indicator chemical composition arranged on the base element, the indicator chemical composition formed from a temperature sensitive material configured to display a base color at a room temperature and change to a first color after being exposed to the first temperature and to a second color after being exposed to the second temperature, wherein the first color is visually distinguishable from the base color, and the second color is visually distinguishable from the base color and the first color;
a wicking material positioned at least in part in contact with the indicator chemical composition;
a film layer positioned over the base element, the wicking material and the indicator chemical composition;
a first pass zone;
a second pass zone; and
a temperature indicator configured to indicate a temperature used in the sterilization cycle;
wherein, the sterilization indicator is configured to indicate that an acceptable level of sterilization has occurred when the indicator chemical composition wicks along the wicking material to a location within the first pass zone after a sterilization cycle using the first sterilization condition, or when the indicator chemical composition wicks along the wicking material to a location within the second pass zone after a sterilization cycle using the second sterilization condition, the temperature indicator displaying a temperature indicator base color at a room temperature and changing to a temperature indicator first color after being exposed to the first temperature and to a temperature indicator second color after being exposed to the second temperature, wherein the temperature indicator first color is visually distinguishable from the temperature indicator base color, and the temperature indicator second color is visually distinguishable from the temperature indicator base color and the temperature indicator first color.

2. The sterilization indicator of claim 1, wherein the base element is formed from a thermally conductive material having a length and a width, and includes a recess formed therein extending along about a longitudinal centerline thereof, wherein the recess is formed within the base material less than the length and the width of the base material; wherein the sterilization indicator further includes a first adhesive layer disposed on the base element; wherein the indicator chemical composition deposited in the recess, and the wicking material is positioned at least in part within the recess, wherein the wicking material extends less than the length and width of the base element; wherein the sterilization indicator further includes a paper layer disposed over the film layer and a second adhesive layer disposed between the paper layer and the film layer, wherein the paper layer and the second adhesive layer include a window therein.

3. The sterilization indicator of claim 2, wherein the temperature indicator is printed on the paper layer using a thermochromic ink.

4. The sterilization indicator of claim 1, further comprising at least one color standard displaying the temperature indicator first color and the temperature indicator second color.

5. The sterilization indicator of claim 4, wherein the at least one color standard includes a first color standard displaying the temperature indicator first color with a reference to the first temperature, and a second color standard displaying the temperature indicator second color with a reference to the second temperature.

6. The sterilization indicator of claim 4, wherein the temperature indicator is printed using an irreversible thermochromic ink that gradually changes color over a range of temperature, and wherein the at least one color standard includes a color scale displaying the gradual color change of the irreversible thermochromic ink over a temperature range including the temperature indicator first temperature and the temperature indicator second temperature, wherein the color standard includes references to at least the temperature indicator first temperature and the temperature indicator second temperature.

7. The sterilization indicator of claim 1, wherein the indicator chemical composition contains a temperature sensitive material and a dye.

8. The sterilization indicator of claim 1, wherein the film layer is formed from a cast polypropylene having a thickness of about 0.9 to 1.1 mil, a thickness of about 2.0 to 2.2 mils, or a thickness of about 3.0 to 3.2 mils, and the base element is aluminum having a thickness of about 3 mils, and the wicking material is formed from a wicking paper having a basis weight of about 66 $g/m^2$ to about 186 $g/m^2$.

9. The sterilization indicator of claim 2, wherein the first adhesive layer is formed from an acrylic adhesive, and the second adhesive layer is formed from an acrylic adhesive.

10. The sterilization indicator of claim 2, wherein the paper layer includes a first marker and a second marker, wherein the first maker is longitudinally spaced from the indicator chemical composition with a first distance therebetween, and the second marker is longitudinally spaced from the indicator chemical composition with a second distance therebetween, wherein the second distance is greater than the first distance.

11. The sterilization indicator of claim 10, wherein the first pass zone is defined by the location of the first marker and an area beyond the first marker, and the second pass zone is defined by the location of the second marker and an area beyond the second marker.

12. The sterilization indicator of claim 1, wherein the first temperature is 121° C. and the first time is selected from 12 minutes, 15 minutes, 20 minutes, and 30 minutes, and the second temperature is 132° C. and the second period of time is 4 minutes, or the second temperature is 134° C. and the second period of time is selected from 3.5 minutes, 4 minutes, 5 minutes and 7 minutes, or the second temperature is 135° C. and the second period of time is 3 minutes.

13. The sterilization indicator of claim 10 further including a third marker, wherein the first pass zone is defined by an area between the first marker and the second marker, and the second pass zone is defined by an area between the second marker and the third marker, wherein the indicator is configured to indicate an acceptable level of sterilization after a sterilization cycle using the first sterilization condition when the indicator chemical composition wicks to a location within the first pass zone and does not wick beyond the second marker, wherein at least a portion of the first pass zone is colored with the temperature indicator first color, and at least a portion of the second pass zone is colored with the temperature indicator second color.

14. The sterilization indicator of claim 13, wherein the film layer is formed from a cast polypropylene having a thickness of about 2.2 mil, and the wicking material is formed from a wicking paper having a basis weight of about 87.7 $g/m^2$ and a thickness of about 7.5 mil.

15. The sterilization indicator of claim 14, wherein the first sterilization condition is selected from 12 minutes at 121° C., 15 minutes at 121° C., 20 minutes at 121° C., 30 minutes at 121° C., and the second sterilization condition is selected from 4 minutes at 132° C., 3.5 minutes at 134° C., 4 minutes at 134° C., 5 minutes at 134° C., 7 minutes at 134° C., and 3 minutes at 135° C.

16. The sterilization indicator of claim 13, wherein the film layer is formed from a cast polypropylene having a thickness of about 2.2 mil, and the wicking material is formed from a wicking paper having a basis weight of about 66 g/m$^2$ and a thickness of about 7.3 mil.

17. The sterilization indicator of claim 16, wherein the first temperature is 121° C. and the first time is 12, 15, 20, or 30 minutes, and the second temperature is 132° C. and the second time is 4 minutes.

18. A steam sterilization indicator configured as a Class 5/Type 5 steam sterilization indicator comprising:
 a base element;
 an indicator chemical composition arranged on the base element, the indicator chemical composition formed from a temperature sensitive material configured to display a base color at a room temperature and change to a first color after being exposed to the first temperature and to a second color after being exposed to the second temperature, wherein the first color is visually distinguishable from the base color, and the second color is visually distinguishable from the base color and the first color;
 a wicking material positioned at least in part in contact with the indicator chemical composition;
 a film layer positioned over the base element, the wicking material and the indicator chemical composition;
 a pass zone and a fail zone; and
 a temperature indicator formed from an irreversible thermochromic ink configured to indicate a temperature of a sterilization cycle,
the thermochromic ink displaying a base color at a room temperature and changing to a first color after being exposed to the first temperature and to a second color after being exposed to the second temperature, wherein the first color is visually distinguishable from the base color, and the second color is visually distinguishable from the base color and the first color.

* * * * *